United States Patent [19]

Mair

[11] Patent Number: 6,130,354
[45] Date of Patent: Oct. 10, 2000

[54] PROCESS FOR THE PREPARATION OF SHIKIMIC ACID AND ITS DERIVATIVES

[75] Inventor: Hans-Jürgen Mair, Lörrach, Germany

[73] Assignee: Hoffman-La Roche Inc., Nutley, N.J.

[21] Appl. No.: 09/307,684

[22] Filed: May 10, 1999

[30] Foreign Application Priority Data

May 13, 1998 [EP] European Pat. Off. .............. 98108655

[51] Int. Cl.$^7$ .................................................... C07C 62/00
[52] U.S. Cl. ............................................ 562/508; 560/126
[58] Field of Search ............................... 562/508; 560/126

[56] References Cited

FOREIGN PATENT DOCUMENTS

WO 96/26933  9/1996  WIPO .
WO 98/07685  2/1998  WIPO .

OTHER PUBLICATIONS

H.J. Bestmann et al., Angew. Chem., vol. 83, 329–331 (1971).

H.J. Bestmann et al., Angew. Chem. Internat. Edit., vol. 10, No. 5, pp. 336–337 (1971).

C.D. Snyder et al., Journal of the American Chemical Society, vol. 95, pp. 7821–7828 (1973).

R. Grewe et al., Chem. Ber., vol. 98, pp. 104–110 (1965) (In German).

J.C. Rohloff et al., J. Org. Chem., vol. 63, pp. 4545–4550 (1998).

Patent Abstracts of Japan, vol. 099, No. 004, JP 11021267 (Apr. 30, 1999).

Fieser et al., "Reagents for Organic Synthesis", pp. 286–289 (1967).

Chem. Abstract *104* (1986) 686825.

Chem Abstract *100* (1984) 51419.

*Primary Examiner*—Paula J. Killos
*Attorney, Agent, or Firm*—George W. Johnston; Patricia S. Rocha-Tramaloni

[57] ABSTRACT

The present invention discloses a process for the preparation of shikimic acid or its derivatives from quinic acid or its derivatives by dehydration with Vilsmeier reagent. The present invention further discloses intermediates produced by this process and their use in the synthesis of shikimic acid or its derivatives.

20 Claims, No Drawings

PROCESS FOR THE PREPARATION OF SHIKIMIC ACID AND ITS DERIVATIVES

FIELD OF INVENTION

The present invention relates to a process for the preparation of shikimic acid [3R-(3α,4α,5β)]-(3,4,5-trihydroxy-1-cyclohexene-1-carboxylic acid) and its derivatives from quinic acid [1R-(1α,3α,4α,5α)]-(1,3,4,5-tetrahydroxy-cyclohexanecarboxylic acid) and its corresponding derivatives.

BACKGROUND OF INVENTION

Shikimic acid and its derivatives are compounds well known in the art and can be prepared according to known methods from corresponding quinic acid derivatives by dehydration using, e.g., $POCl_3$ in pyridine (Bestmann, H. . et al., Angew. Chemie 83, 329 [1971]; Snyder, C. D. et al., J. Am. Chem. Soc. 95, 7821 [1973]; Grewe R. et al., Chem. Ber. 98, 104 [1965]) or $SO_2Cl_2$ in pyridine (Snyder, loc. cit.; WO 98/07685).It has now surprisingly been found that higher regioselectivity of the dehydration than described in the state of the art (up to 6:1, see Rohloff J. C., J. Org. Chem., 63:4545 (1998)) can be achieved by using $ClCH=N^+ (CH_3)_2Cl^-$ (Vilsmeier reagent) as the dehydration reagent. The degree of regioselectivity according to the present invention is very high, e.g., in the range of 50:1 and can be as high as 100:1 for the desired stereoisomer.

SUMMARY OF INVENTION

The present invention relates to a process for the preparation of shikimic acid and its derivatives by dehydration of quinic acid and its derivatives using Vilsmeier reagent.

In one embodiment, the Vilsmeier reagent utilized in the process of the invention is commercially available Vilsmeier reagent. In an alternative embodiment, the Vilsmeier reagent utilized in the process of the invention is produced in situ.

The invention therefore relates to shikimic acid and derivatives thereof produced by the process of the invention.

The invention further relates to intermediates produced by the process of the invention and the use of those intermediates in the synthesis of shikimic acid and its derivatives.

DETAILED DESCRIPTION OF INVENTION

The present invention is directed to a process of using Vilsmeier reagent to produce shikimic acid or its derivatives from quinic acid or its derivatives where quinic acid is

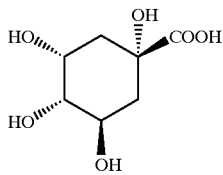

and derivatives of quinic acid comprise all derivatives obtainable by modification of one, several or all functional groups except the hydroxy group in 1-position, especially those quinic acid derivatives having a protected carboxylic group and/or at least one of the three adjoining hydroxy groups in protected form and corresponding salts. Where two adjoining hydroxy groups are to be protected, they can be protected separately by the same protecting group or by different protecting groups, or, jointly by a 1,2-diol protecting group. When the hydroxy groups in the 3- and 4-positions or the 4- and 5-positions are to be protected by a 1,2-diol protecting group, the hydroxy group in the 5- or 3-position respectively may either be unprotected or protected by a different protecting group.

In a specific embodiment of the present invention, quinic acid (or a derivative thereof) used as a starting material in the process of the invention is a compound of formula

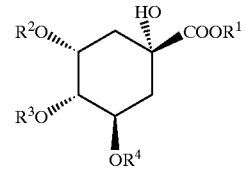

I or a salt thereof wherein
$R^1$ is hydrogen or a carboxylic acid protecting group,
$R^2$ is hydrogen or a hydroxy protecting group,
$R^3$ is hydrogen or a hydroxy protecting group or
$R^2$ and $R^3$, taken together are a 1,2-diol protecting group, and
$R^4$ is hydrogen or a hydroxy protecting group.

By the terms carboxylic acid and hydroxy protecting groups (including 1,2 diol protecting groups) as used above is meant the very large number of carboxylic acid and hydroxy protecting groups (including 1,2-diol protecting groups) and corresponding chemical cleavage reactions known to the person skilled in the art and described, e.g., in "Protective Groups in Organic Chemistry", Theodora W. Greene et al. (John Wiley & Sons, Inc., New York, 1991) or in "Protecting Groups", Philip J. Kocienski (Georg Thieme Verlag Stuttgart, New York, 1994, both which are hereby incorporated by reference in particular Chapter 1, Protecting Groups: An Overview, pages 1–20, Chapter 2, Hydroxyl Protecting Groups, pages 21–94, Chapter 3, Diol Protecting Groups, pages 95–117, Chapter 4, Carboxyl Protecting Groups, pages 118–154).)

Typically a carboxylic acid group is protected in the form of an ester group. In one embodiment, $R^1$ is a carboxylic acid protecting group which is alkyl of 1 to 12 carbon atoms, alkenyl of 2 to 12 carbon atoms, or alkynyl of 2 to 12 carbon atoms, any one of which alkyl, alkenyl, or alkynyl may be substituted with 0–3 groups as defined, e.g., in WO 98/07685, which is hereby incorporated by reference. In a more preferred embodiment, a $R^1$ is a carboxylic acid protecting group which is alkyl of 1 to 6 carbon atoms, alkenyl of 2 to 6 carbon atoms, or alkynyl of 2 to 6 carbon atoms, any one of which alkyl, alkenyl, or alkynyl may be substituted with 0–3 groups as defined in the above mentioned WO. In yet a more preferred embodiment, $R^1$ is a carboxylic acid protecting group which alkyl of 1 to 8 carbon atoms substituted with 0–2 groups as defined in the above mentioned WO. Even more typically, $R^1$ is alkyl of 1, 2, 3, 4, 5, 6, 7, or 8 carbon atoms. In a most preferred embodiment a $R^1$ is a carboxylic acid protecting group which is methyl, ethyl, 1-propyl or 2-propyl.

Typically a hydroxy group is protected in the form of an ether or ester. Therefore, a $R^2$, $R^3$ or $R^4$ hydroxy protecting group includes, but is not limited to, methyl, substituted methyl, ethyl, substituted ethyl, benzyl, substituted benzyl or substituted silyl, such as trialkyl silyl. Examples of suitable esters are formates, benzoylformates, acetates, chloroacetates, dichloroacetates, trichloroacetates, trifluoroacetates, methoxyacetates, benzoates, carbonates and sulfonates, such as sulfates, methanesulfonates (mesylates), benzylsulfonates and tosylates.

Typical 1,2-diol protecting groups are described in Greene at pages 118–142 and mentioned in WO 98/07685 and include, but are not limited to, groups forming cyclic acetals and ketals (e.g. methylene, ethylidene, 1-t-butylethylidene, 1-phenylethylidene, (4-methoxyphenyl)-ethylidene, 2,2,2-trichloroethylidene, isopropylidene, cyclopentylidene, cyclohexylidene, cycloheptylidene, benzylidene, p-methoxybenzylidene, 2,4-dimethoxybenzylidene, 3,4-dimethoxybenzylidene, 2-nitrobenzylidene); cyclic ortho esters (e.g. methoxymethylene, ethoxymethylene, dimethoxymethylene, 1-methoxyethylidene, 1-ethoxyethylidene, 1,2-dimethoxyethylidene, α-methoxybenzylidene), silyl derivatives (e.g. di-t-butylsilylene), cyclic carbonates, cyclic boronates, ethyl boronate and phenyl boronate. Preferred 1,2-diol protecting groups are alkylidene, especially alkylidene with 1–6 carbon atoms, isopropylidene being most preferred.

In preferred specific embodiments of the present invention, quinic acid or derivatives thereof to be dehydrated are compounds of formula I wherein $R^1$ is hydrogen; compounds of formula I wherein $R^1$ is alkyl; compounds of formula I wherein $R^2$, $R^3$ and $R^4$ are hydrogen; compounds of formula I wherein at least one of $R^2$, $R^3$ and $R^4$ is a hydroxy protecting group where the protecting group(s) is (are) preferably an acyl and/or alkyl group(s); compounds of formula I wherein $R^2$ and $R^3$ together represent an alkylidene group; compounds of formula I wherein $R^2$ and $R^3$ together represent an alkylidene group and $R^4$ is an acyl group; compounds of formula I wherein $R^2$ and $R^3$ together represent an alkylidene group and $R^4$ is a sulfonic acid residue; and compounds of formula I wherein $R^1$ is ethyl, $R^2$ and $R^3$ are isopropylidene and $R^4$ is mesyl.

In the process of the invention, a compound of formula I or a salt thereof is dehydrated with Vilsmeier reagent to form a corresponding compound of formula

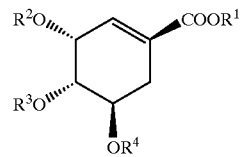

II

Typically the dehydrating process comprises treating quinic acid or a derivative thereof with the Vilsmeier reagent in a suitable solvent, preferably a polar aprotic solvent at a temperature between room temperature and about 100° C., preferably at 50–100° C., more preferably at 50–80° C., for such time as is required for a complete conversion of the starting material, typically a couple of hours. The time of heating depends on the solvent, temperature, and Vilsmeier reagent used and can readily be ascertained by one skilled in the art. Suitable apotic solvents include ethyl acetate, dimethylformamide (DMF), isopropyl acetate, methyl acetate, methylene-chloride, 1,2-dichloroethane, tetrahydrofuran, 1,4-dioxane, tert-butyl methyl ether, toluene, and acetonitrile. In case of ethyl acetate the reaction mixture is preferably heated under reflux. In one embodiment, the Vilsmeier reagent is a commercially available product and can be introduced into the reaction as such. In one embodiment, 1.0–2.0 equivalents of Vilsmeier reagent are used per 1.0 equivalent of quinic acid starting material. In a preferred embodiment, 1.1–1.7 equivalents of Vilsmeier reagent, more preferably 1.1–1.5 equivalents, are used per 1.0 equivalent of quinic acid.

Alternatively the Vilsmeier reagent can be produced in situ from $POCl_3$, oxalyl dichloride or phosgene in DMF. In the latter case a solution of quinic acid or its derivative in DMF is reacted with an excess of $POCl_3$, oxalyl dichloride or phosgene, preferably 1.1–1.5 equivalents, at room temperature for about one hour. The reaction mixture is then heated for several hours to a temperature of about 70° C. During the reaction at room temperature the Vilsmeier reagent reacts with the tertiary hydroxy group to form an intermediate compound which in case of a starting material of formula I is represented by general formula

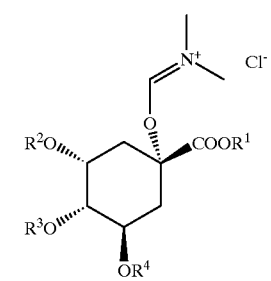

III wherein $R^1$–$R^4$ are as defined above.

During further heating of up to 70° C. the intermediate compound by elimination of DMF is converted into the corresponding shikimic acid or derivative which after neutralization of the reaction mixture can then be isolated and purified using methods well known in the art, such as, for example, those methods as are described in the examples below.

Treatment of the intermediate compounds of formula III with an aqueous solvent yields corresponding quinic acid derivatives wherein the tertiary hydroxy group is formylated. Suitable aqueous solvents include aqueous sodium or potassium hydroxide solution or aqueous sodium hydrogen carbonate or sodium carbonate solutions. These compounds are also an embodiment of the present invention. In case of starting compounds of formula I the compounds obtained via compounds of formula III are compounds of formula

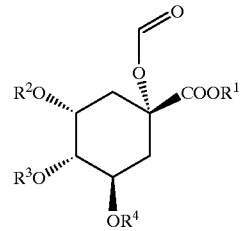

IV wherein $R^1$–$R^4$ are as defined above.

Depending on the specific protecting groups present in the starting material, viz. the quinic acid derivative, and the specific reaction conditions used in the dehydrating reaction, protecting groups may be eliminated or transformed and shikimic acid in unprotected or in partially protected form may be obtained. It is within the general knowledge of the person skilled in the art to manipulate the reaction conditions in the desired direction or to transform a specific shikimic acid derivative of formula II obtained into a different derivative of formula II. In a preferred embodiment according to the invention, the shikimic acid obtained is partially protected, and more preferably, completely protected.

Shikimic acid and its derivatives are intermediates in the synthesis of nown valuable compounds with known industrial applicability, especially of pharmaceutically active compounds (e.g. WO 96/26933 and WO 98/07685, both of which are hereby incorporated by reference).

The following Examples illustrate and describe in more detail the present invention without limiting it.

EXAMPLE 1

In a dried and nitrogen purged reactor 61.4 g of commercially available (Isochem SNPE Pharma, France) Vilsmeier reagent (480 mmol, 1.2 equiv.) are suspended in 112 ml of ethyl acetate. A solution of 135.3 g of 1-hydroxy-3,4-isopropylidenedioxy-5-mesyloxy-cyclohexanecarboxylic acid ethyl ester (=3,4-isopropylidene-5-mesyl-quinic acid ethyl ester; 400 mmol, 1.0 equiv.) in 458 ml ethyl acetate is added at room temperature. The resulting mixture is heated to 70–75° C. until the reaction is finished (about 3 hrs). After cooling the solution is quenched with a mixture of 330.5 g of aqueous sodium hydroxide solution (28%) and 460 g of ice. The organic layer is washed with sodium hydrogen carbonate and water. The combined water layers are back-extracted with ethyl acetate. The combined organic layers are then concentrated under reduced pressure and the residue is crystallized from hot methanol. 75 g (59%) of 3,4-isopropylidene-5-mesyl-shikimic acid ethyl ester are obtained, m.p. 103° C. The regioselectivity was in the range of 50:1.

EXAMPLE 2

In a dried and nitrogen purged reactor 80.0 g of 3,4-isopropylidene-5-mesyl-quinic acid ethyl ester (236 mmol, 1.0 equiv.) are dissolved in 320 ml of dimethylformamide (DMF). Under cooling 47.1 g of phosphorus oxychloride ($POCl_3$; 307 mmol, 1.3 equiv.) are added. The resulting clear solution is stirred for additional 60 minutes at room temperature and then heated to 60–63° C. until the reaction is finished (about 6 hrs). After cooling the solution is quenched with a mixture of 480 ml tert-butyl methyl ether (TBME), 120 ml methylene chloride, and 500 ml of aqueous 2.5N sodium hydroxide solution. The pH-value is adjusted to neutral. The aqueous layer is extracted with a mixture of TBME and methylene chloride. The combined organic layers are washed with sodium hydrogen carbonate and water. The organic layer is concentrated under reduced pressure and the product is crystallized from hot TBME. 42 g (55%) of 3,4-isopropylidene-5-mesyl-shikimic acid ethyl ester are obtained, m.p. 103° C. The regioselectivity was again 50:1.

What is claimed is:

1. A process for preparing shikimic acid or a derivative thereof, said process comprising reacting quinic acid or a derivative thereof with Vilsmeier reagent under conditions suitable to effect dehydration of the quinic acid or its derivatives.

2. The process of claim 1, wherein the quinic acid or derivative thereof to be dehydrated is a compound of formula

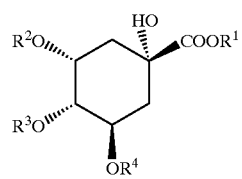

or a salt thereof wherein $R^1$ is hydrogen or a carboxylic acid protecting group, $R^2$ is hydrogen or a hydroxy protecting group, $R^3$ is hydrogen or a hydroxy protecting group or $R^2$ and $R^3$ taken together are a 1,2-diol protecting group, and $R^4$ is hydrogen or a hydroxy protecting group.

3. The process of claim 2, wherein $R^1$ of the compound of formula I is hydrogen.

4. The process of claim 2, wherein $R^1$ of the compound of formula I is a carboxylic acid protecting group.

5. The process of claim 4, wherein the carboxylic acid protecting group is an alkyl group.

6. The process of claim 2, wherein $R^2$, $R^3$ and $R^4$ of the compound of formula I are hydrogen.

7. The process of claim 2, wherein at least one of $R^2$, $R^3$ and $R^4$ of the compound of formula I is a hydroxy protecting group.

8. The process of claim 7, wherein the protecting group(s) is (are) an acyl and/or alkyl group(s).

9. The process of claim 7, wherein $R^2$ and $R^3$ taken together are a 1,2-diol protecting group.

10. The process of claim 9, wherein the 1,2-diol protecting group for $R^2$ and $R^3$ is an alkylidene.

11. The process of claim 10, wherein $R^4$ is a hydroxy protecting group.

12. The process of claim 11, wherein the hydroxy protecting group for $R^4$ is an acyl group.

13. The process of claim 11, wherein the hydroxy protecting group for $R^4$ is a sulfonic acid residue.

14. The process of claim 2, wherein the compound of formula I is 3,4-isopropylidene-5-mesyl-quinic acid ethyl ester.

15. The process of claim 1, wherein the Vilsmeier reagent used in said process is commercially available Vilsmeier reagent.

16. The process of claim 15, wherein the quinic acid or derivative thereof is reacted with Vilsmeier reagent in a polar aprotic solvent.

17. The process of claim 16, wherein the polar aprotic solvent is ethyl acetate.

18. The process of claim 1, wherein the Vilsmeier reagent used in said process is formed in situ with $POCl_3$, oxalyl dichloride or phosgene in dimethylformamide.

19. An intermediate compound or a salt thereof produced according to the process of claim 2, wherein said compound has the formula

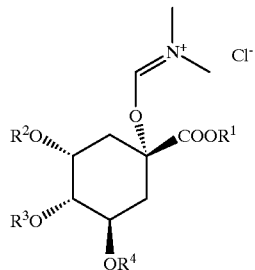

III wherein
$R^1$ is hydrogen or a carboxylic acid protecting group,
$R^2$ is hydrogen or a hydroxy protecting group,
$R^3$ is hydrogen or a hydroxy protecting group or
$R^2$ and $R^3$ taken together are a 1,2-diol protecting group, and
$R^4$ is hydrogen or a hydroxy protecting group.

20. A process for preparing a compound of formula

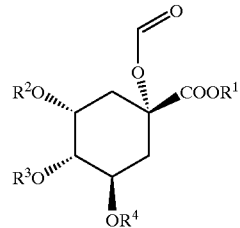

IV or a salt thereof, wherein
$R^1$ is hydrogen or a carboxylic acid protecting group,
$R^2$ is hydrogen or a hydroxy protecting group,
$R^3$ is hydrogen or a hydroxy protecting group or
$R^2$ and $R^3$ taken together are a 1,2-diol protecting group, and
$R^4$ is hydrogen or a hydroxy protecting group,
said process comprising treating the compound of claim 21 with an aqueous solvent under conditions suitable to produce the compound of formula IV.

* * * * *

UNITED STATES PATENT AND TRADEMARK OFFICE
CERTIFICATE OF CORRECTION

PATENT NO.    : 6,130,354  
DATED         : October 10, 2000  
INVENTOR(S)   : Hans-Jürgen Mair It is certified that error appears in the above-identified patent and that said Letters Patent is hereby corrected as shown below:

<u>Column 8,</u>
Line 22, delete "21" and insert -- 19 --

Signed and Sealed this

Twenty-fifth Day of March, 2003

JAMES E. ROGAN
*Director of the United States Patent and Trademark Office*